(12) United States Patent
Huybrechts

(10) Patent No.: US 6,646,153 B1
(45) Date of Patent: Nov. 11, 2003

(54) HYDROXYL FUNCTIONAL URETHANES HAVING A TERTIARY CARBAMATE BOND

(75) Inventor: Josef Huybrechts, Oud-Turnhout (BE)

(73) Assignee: E. I. du Pont de Nemours and Company, Wilmington, DE (US)

(*) Notice: Subject to any disclaimer, the term of this patent is extended or adjusted under 35 U.S.C. 154(b) by 0 days.

(21) Appl. No.: 09/619,320

(22) Filed: Jul. 19, 2000

(51) Int. Cl.$^7$ ............................................. C07C 27/100
(52) U.S. Cl. ........................................................ 560/158
(58) Field of Search ......................................... 560/158

(56) References Cited

U.S. PATENT DOCUMENTS

| | | | | |
|---|---|---|---|---|
| 4,177,342 A | * | 12/1979 | Bock et al. | 528/45 |
| 4,485,228 A | | 11/1984 | Chang et al. | 528/84 |
| 4,540,766 A | | 9/1985 | Chang et al. | 528/45 |
| 4,540,771 A | | 9/1985 | Ambrose et al. | 528/272 |
| 4,542,173 A | | 9/1985 | Schupp et al. | 523/414 |
| 4,543,405 A | | 9/1985 | Ambrose et al. | 528/78 |
| 4,605,724 A | | 8/1986 | Ambrose et al. | 528/73 |
| 4,820,830 A | | 4/1989 | Blank | 560/158 |
| 4,883,854 A | | 11/1989 | Coury et al. | 528/28 |
| 5,130,405 A | | 7/1992 | Walker et al. | 528/78 |
| 5,175,227 A | | 12/1992 | Gardon et al. | 528/45 |
| 5,175,231 A | | 12/1992 | Rappoport et al. | 528/106 |
| 5,977,262 A | * | 11/1999 | Anderson | 525/327.2 |

FOREIGN PATENT DOCUMENTS

| | | |
|---|---|---|
| EP | 0 661 316 A1 | 7/1995 |
| EP | 0 767 187 A1 | 4/1997 |
| EP | 0 767 227 A1 | 4/1997 |
| EP | 0 767 228 A1 | 4/1997 |
| EP | 0 767 230 A1 | 4/1997 |
| EP | 0 767 231 A1 | 4/1997 |
| EP | 0 767 232 A2 | 4/1997 |
| EP | 0 767 229 A1 | 9/1997 |
| EP | 0 866 082 A1 | 9/1998 |
| EP | 0 767 226 B1 | 8/1999 |
| WO | WO-97/00851 | * 2/1987 ............ C09D/7/12 |

* cited by examiner

Primary Examiner—Ceila Chang
Assistant Examiner—Taylor V. Oh
(74) Attorney, Agent, or Firm—Bart E. Lerman

(57) ABSTRACT

Hydroxy functional urethane compounds comprising the reaction product of a hydroxy functional urethane intermediate with a compound having at least 2 isocyanate groups, wherein the intermediate is represented by the formula:

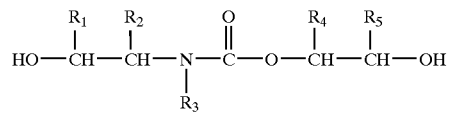

wherein
- $R_1$ and $R_2$=hydrogen, alkyl, cycloalkyl or a residue $R_6$—O— or $R_6$—CO—O— with $R_6$;
- $R_6$=an alkyl, cycloalkyl or benzylic group having up to 18 carbon atoms;
- $R_4$ and $R_5$=hydrogen or alkyl group containing eventually a hydroxyl group; and
- $R_3$=alkyl, cycloalkyl or benzylic group eventually containing an ether linkage and/or a hydroxyl group, or HO—CH($R_1$)—CH($R_2$)—;

and is prepared by reaction of a cyclic 5-ring carbonate with a beta-hydroxy functional, secondary amine. The hydroxy functional urethanes are useful in paints and coatings, particularly for automotive applications.

7 Claims, No Drawings

HYDROXYL FUNCTIONAL URETHANES HAVING A TERTIARY CARBAMATE BOND

BACKGROUND OF THE INVENTION

This invention relates to novel reactive urethane compounds, their synthesis and end-uses particularly in automotive coatings with improved chemical resistance and mechanical properties. In a preferred embodiment, the invention relates to automotive paint compositions having hydroxy functional binders and a cross-linking agent such as melamine, urea or benzoguanamine formaldehyde resins (so called aminoplast resins) and/or blocked polyisocyanates (when the curing temperature is relatively high, i.e., above 80° C.) in a one-pack formulation or polyisocyanates (when the crosslinking needs to take place at lower temperatures) in 2-pack formulations.

Acrylic polyols are typically used in topcoat formulation because of the outstanding durability. However,the mechanical properties like chip resistance and scratch resistance are poor. Polyester polyols do give better mechanical properties but are poor for chemical resistance, specifically acid etch resistance. Polyurethane polyols combine excellent chemical and mechanical properties with very good durability.

U.S. Pat. Nos. 4,485,228 and 4,540,766 describe high solids coating systems based on low molecular weight polyester urethane polyols. More particularly U.S. Pat. No. 4,485,228 describes compositions crosslinked with polyisocyanates in a 2-pack system while U.S. Pat. No. 4,540,766 describes 1-pack systems crosslinked with polyisocyanates. In those patents the polyester urethane polyols are prepared by a stoichiometric excess of a polyester polyol with a polyisocyanate to avoid high molecular weight build-up during the synthesis.

U.S. Pat. No. 4,543,405 refers to low molecular weight polyurethane polyols which are prepared from a polyisocyanate with a large excess of a polyol. This excess of polyol is, after the reaction has completed, distilled-off. In related U.S. Pat. Nos. 4,540,771 and 4,605,724 the polyester polyols for the polyurethane polyols are produced from polycarboxylic acids or lactone with low molecular weight polyol, wherein the excess polyol is also removed by distillation. The disadvantage of the procedure in above mentioned references is the distillation step which is not economic.

EP 0 661 316 and EP 0 866 082 relate to reactive urea/urethane compounds, the process for preparation and coatings based on those compounds which are prepared from the reaction of a polyisocyanate with a secondary amine containing one or two hydroxyl groups. The advantage of this process is the fact that the reaction of the isocyanate group preferentially goes with the secondary amine group to form low molecular weight hydroxyfunctional urethane-urea adducts. The disadvantage is that urea groups have a strong hydrogen bonding character which leads to limited solubility and relatively high solution viscosity. U.S. Pat. No. 5,130,405 and U.S. Pat. No. 5,175,227 are directed to high solids coating compositions containing polyurethane oligomers derived from the reaction of symmetrical and unsymmetrical 1,3-diols and polyisocyanates. Such compounds do have very low molecular weight with high hydroxyl values. Low molecular weight oligomers with high hydroxyl values act as strong slow solvents and many times negatively influence the appearance of automotive clear coats. EP 0 767 230, EP 0 767 187, EP 0 767 226, EP 0 767 228, EP 0 767 231, EP 0 767 229, EP 0 767 232 and EP 0 767 227 all relate to curable coating compositions having carbamate functional groups for crosslinking purposes. The carbamate functional groups can be represented by

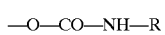
—O—CO—NH—R wherein R is hydrogen or alkyl, preferably Cl -C4 alkyl and more preferably hydrogen. Primary carbarnates (R=hydrogen) negatively influence solution viscosity due to strong hydrogen bonding and secondary carbamates need specific catalysis to react with amino resins.

U.S. Pat. No. 4,820,830 relates to hydroxyalkyl carbamates prepared by reacting cyclic carbonates with diamines. Such hydroxyalkyl carbamates have many times limited solubility and compatibility due to high secondary carbamate content. U.S. Pat. No. 4,883,854 describes polyurethanes derived from hydroxyalkyl carbamates which are synthesized from polyamines with at least two amine groups and cyclic carbonates. There is no teaching on the reaction products of mono secondary amines with cyclic carbonates to form the hydroxyl functional carbamates and the further use in the synthesis of branched hydroxyl functional oligomers with controlled molecular weight distribution. U.S. Pat. No. 4,542,173 relates to self-crosslinkable binders containing at least to hydroxyalkyl carbamate groups with a secondary carbamate group. U.S. Pat. No. 5,175,231 relates to urethane oligomers with an amine functional group.

It is therefore desirable to find a method for preparing highly branched hydroxy functional urethane adducts with a controlled molecular weight distribution and essentially free from primary carbamate and urea groups. Such compounds would provide coating compositions with a good combination of low solution viscosity (low VOC), excellent chemical resistance, mechanical properties and outdoor durability.

SUMMARY OF THE INVENTION

Hydroxy functional urethane compounds comprising the reaction product of:

a) a hydroxy functional urethane intermediate containing a tertiary carbamate group prepared by reaction of a cyclic 5-ring carbonate with a beta-hydroxy functional, secondary amine, said intermediate represented by the formula:

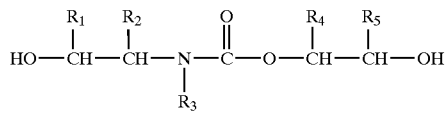

wherein
$R_1$ and $R_2$=hydrogen, alkyl, cycloalkyl or a residue $R_6$—O— or $R_6$—CO—O— with $R_6$;
$R_6$ =an alkyl, cycloalkyl or benzylic group having up to 18 carbon atoms;
$R_4$ and $R_5$=hydrogen or alkyl group containing eventually a hydroxyl group; and R₃=alkyl, cycloalkyl or benzylic group eventually containing an ether linkage and/or a hydroxyl group, or HO—CH(R₁)—CH(R₂)— with b) a compound with at least 2 isocyanate groups.

Such hydroxy functional urethanes can be used in automotive coatings to improve the mechanical properties and chemical resistance of such coatings.

DETAILED DESCRIPTION OF THE INVENTION

The present invention relates to novel hydroxyl functional binders which comprise the reaction product of polyisocyanates with a tertiary carbamate having at least two hydroxyl groups. The coating compositions based on those binders offer improved mechanical properties and chemical resistance. The tertiary carbamate with at least two hydroxyl groups can be represented as:

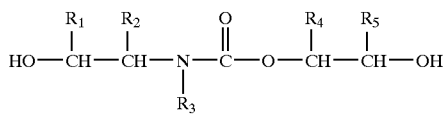

wherein

R₁ and R₂=hydrogen, alkyl, cycloalkyl or a residue R₆—O— or R₆—CO—O— with R₆;

R₆=an alkyl, cycloalkyl or benzylic group having up to 18 carbon atoms;

R₄ and R₅=hydrogen or alkyl group containing eventually a hydroxyl group; and

R₃=alkyl, cycloalkyl or benzylic group eventually containing an ether linkage and/or a hydroxyl group, or HO—CH(R₁)—CH(R₂)—

In particularly preferred embodiments, R₁ is CH₃ or H; R₂ is H, R₃ is HO—CH(CH₂)—CH₂— or CH₃(CH₂)₃—; R₄ is H; and R₅ is H, CH₃, or C₂H₅.

Such carbamates can be prepared by the reaction of a secondary amine with a cyclic 5-ring carbonate. Examples of 5-ring carbonates include ethylene carbonate, propylene carbonate, butylene carbonate and glycerine carbonate. Examples of secondary amines are alkyl, benzyl and cycloalkyl-ethanolamines and alkyl-propanol amines as methyl ethanolamine, n-butyl aminoethanol, hexyl aminoethanol, benzyl aminoethanol, cyclohexyl aminoethanol, methyl propanolamine, n-butyl propanolamine, cyclohexyl propanolamine and benzyl propanolamine.

Such compounds are typically prepared by reaction of cyclic oxides as ethyleneoxide or propyleneoxide with a primary amine. Examples of bis-hydroxyl functional secondary amines are diethanolamine and diisopropanolamine. Secondary amines can also be prepared from the reaction of primary amines with other cyclic three-member oxides as n-butyleneoxide, cyclohexeneoxide, i-butyleneoxide and derivatives as monoepoxy ethers and monoepoxy esters. Examples of monoepoxy esters are glycidyl esters of mono acids as acetic acid, butyric acid, isobutyric acid, pivalic acid, versatic acid and C9 and C10 alpha branched fatty acids available from Shell. Examples of monoepoxy ethers are glycidyl ethers of phenyl, n-butyl, lauryl, t-butylphenyl and cyclohexyl.

The reaction of the secondary amine can be performed at room temperature up to 200° C., preferably between 40° C. and 150° C. Solvents can eventually be used in this reaction. Examples of solvents are alcohols, ketones, esters, amides, and aliphatic or aromatic hydrocarbons. Typical examples are methanol, n-butanol, s-butanol, t-butanol, n-propanol, i-propanol, n-hexanol, 2-ethyl hexanol, laurylalcohol, acetone, methyl ethyl ketone, isobutyl methyl ketone, methyl amyl ketone, toluene, xylene, Solvesso® 100, Solvesso® 150, Solvesso® 200 (trade name of Exxon Corporation), heptane, mineral spirits, n-methyl pyrrolidone, ethylacetate, n-butylacetate, i-butylacetate, t-butylacetate, 2-ethyl hexylacetate, propylene glycol, ethylene glycol, propylene glycol n-butyl ether, propylene glycol n-butyl ether acetate, diethylene glycol and diethyleneglycol diacetate.

Catalysts can be used in the synthesis of the tertiary carbamate intermediate as e.g., tin and zinc salts (dibutyl tin dilaurate, dibutyl tin oxide, tin octoate, zinc octoate), bases (potassium hydroxide, sodium hydroxide, magnesium hydroxide) and acids (acetic acid, toluene sulfonic acid, dodecyl benzene sulfonic acid, phenyl acid phosphate).

In a next step, the hydroxyl functional tertiary carbamate intermediate is reacted with a compound having at least two isocyanate groups. Example of such compounds are diisocyanates as e.g., hexamethylene diisocyanate, isophorone diisocyanate, toluene diisocyanate, 3,3',5-trimethyl hexamethylene diisocyanate, meta and para tetramethyl xylene diisocyanate, 4,4'-dicyclohexylmethane diisocyanate (Desmodur® W from Bayer AG) and 4,4'-diphenylmethane diisocyanate. Polyfunctional isocyanates derived from the diisocyanates can also be used as e.g., the cyclotrimer of isophorone diisocyanate and hexamethylene diisocyanate, the biuret of hexamethylene diisocyanate, the uretdion dimer of hexamethylene diisocyanate (i.e., the 4 ring dimerization product of NCO with NCO), the adducts of polyols (e.g., trimethylol propane) with an excess of diisocyanate.

A polyisocyanate can also be formed by reaction of a diisocyanate excess with a compound having at least two reactive groups versus the isocyanate, preferably having at least two hydroxyl groups. Such compounds can be diols or polyols derived from polyesters, polycarbonates, polyethers, polyacrylics and polyisocyanates.

The novel urethanes which are the final reaction products of the tertiary carbamate intermediate with the polyisocyanates can be used in paint compositions in which the reaction product is crosslinked with an amino resin or polyisocyanate which can be blocked or unblocked. It has been found that cured films from above paint compositions have good chemical resistance and mechanical properties like hardness, flexibility, scratch and chip resistance. Specifically, automotive clearcoats made with these novel urethanes demonstrate significant improvements in acid etch and scratch resistance. In one pack clearcoats the crosslinkers are typically melamine formaldehyde adducts etherified with alcohols as methanol, isobutanol or n-butanol. Blocked polyisocyanates can also be used as e.g., methylethyl ketoxime or dimethyl pyrazole blocked trimers of hexamethylene diisocyanate or isophorone diisocyanate. In such one pack clearcoats, the curing temperature is above 80° C. typically between 100° C. and 180° C. The clearcoats may contain additives to improve properties as e.g., application (sagging), flow, wetting, durability. Other polymers can be used in the clearcoats to improve specific properties which include acrylics, polyesters, vinyls, polyurethanes, polycarbonates, alkyds and polysilanes.

Catalysts can be added to speed-up the curing reaction as e.g. toluene sulfonic acid, phenyl acid phosphate, dibutyl tin dilaurate. Other one pack automotive paint compositions include primers, basecoats and pigmented topcoats. Those compositions contain regular pigments and extenders which can be organic or inorganic. Examples of pigments include titanium dioxide, barium sulfate, talc, aluminum silicate, phtalocyanines, quinacridones, carbon black, aluminum flakes, mica flakes and lead chromate. In refinish applications, the curing temperature of the final coating is ambient up to 80° C. maximum. The reaction products of the present invention can be used is two pack coatings in which the crosslinker is added to the paint containing the reaction product prior to application. Typical crosslinkers used in two component paints are polyisocyanates. Specific examples are the biuret and cyclotrimer of hexamethylene diisocyanate and isophorone diisocyanate.

Coating compositions can be coated on the article by any number of techniques well-known in the art. These include, for example, spray coating, dip coating, roll coating, curtain coating and the like. For automotive body panels, spray coating is preferred. The substrate can be any substrate onto which a coating formulation can be applied and cured. Preferably the substrate is a metallic or polymeric panel suitable as an automotive body panel.

EXAMPLES

The invention is further described in the following examples. Comparative examples demonstrate the difference from the prior art. Molecular weights are determined by gel permeation chromatography using polystyrene as standards. Percent solids is determined gravimetrically by the weight difference of the sample after drying in an oven for 1 hour at 105° C. Amine and acid values are determined by titration and viscosity by Gardner-Holdt tubes.

Examples 1–3

Synthesis of Tris Hydroxyl Functional Urethane Intermediate With Tertiary Urethane Bonds The following reactants (in grams) were mixed and refluxed in a 500 ml reactor equipped with a condenser, heating mantle and stirrer until the amine value was constant.

| | Example | | |
|---|---|---|---|
| | 1 | 2 | 3 |
| Diisopropanolamine | 133 | 133 | 133 |
| Ethylenecarbonate | 90 | | |
| Propylenecarbonate | | 104 | |
| Butylenecarbonate | | | 118 |
| Methylisobutyl ketone | 92 | 98 | 104 |

The reflux temperature was 126° C. for 1, 140° C. for 2 and 143° C. for 3. After 12 hours reflux, the amine value was 16 for 1, 19 for 2 and 16 for 3. Example 1 is a tris hydroxy functional urethane intermediate with 1 primary and 2 secondary hydroxyl groups while examples 2 and 3 contain all secondary hydroxyl groups.

Examples 4–8

Reaction of Tris Hydroxyl Functional Intermediate With Cyclotrimers to Branched Urethane Oligomers In a 1 liter reactor equipped with a funnel, stirrer, condenser and heating mantle, the reaction products of Example 1 and 2 above were mixed with butylacetate in Part 1. In Part 2, the cyclotrimer of isophoronediisocyanate (IPDI trimer, available from Creanova-Huls as IPDI T-1890) or the cyclotrimer of hexarnethylenediisocyanate (HDI trimer, available from Bayer AG as Desmodur® 3390) was added followed by a rinsing step of butylacetate. The contents of the reactor were refluxed for about 1 hour until the isocyanate peak in the IR spectra at about 2200 $cm^{-1}$ had disappeared. All amounts are in grams. The molar ratio of tris hydroxy functional intermediate to cyclotrimer in all examples was 3:1.

| | Example: | | | | |
|---|---|---|---|---|---|
| | 4 | 5 | 6 | 7 | 8 |
| Part 1: | | | | | |
| Example 1 | 315 | | 315 | | |
| Example 2 | | 335 | | 335 | |
| Example 3 | | | | | 355 |
| Butylacetate | 100 | 100 | | | 100 |
| Part 2: | | | | | |
| IPDI trimer | 350 | 350 | | | 350 |
| HDI trimer | | | 210 | 210 | |
| Butylacetate (Rinse) | 11 | 15 | 60 | 60 | 18 |
| Test Results | | | | | |
| Solids content % | 60.3 | 59.4 | 69.6 | 68.5 | 63.9 |
| Viscosity gardner-holdt | T + 1/2 | R– | X | U + 1/2 | Y – 1/4 |
| Number average MW | 2100 | 1900 | 3300 | 2700 | 2000 |
| Weight average MW | 4300 | 3300 | 10400 | 6400 | 3400 |
| Dispersity | 2 | 1.7 | 3.4 | 2.4 | 1.7 |

All reaction products were light in color and did not contain any gelled material.

Comparative Examples 1–4

Reaction of Tris Hydroxyl Intermediates With Cyclotrimers

Following the procedure of examples 4–8, it was attempted to prepare a branched urethane oligomer from three moles of a tris hydroxy functional intermediate without a urethane linkage and 1 mole of a cyclotrimer. The tris hydroxy functional intermediate in comparative examples 1 and 2 was Polyol® TP 30 from Perstorp, which is the ethoxylated reaction product of trimethylolpropane (TMP) (molar TMP/ethylene oxide=⅓) with molecular weight +−270 and hydroxyl value 623 with three primary hydroxyl groups.

In comparative example 3,4 it was Polyol® TS30 which is the propoxylated reaction product of TMP (molar TMP/propylene oxide=⅓) with molecular weight +−311 and hydroxyl value 542 with three secondary hydroxyl groups.

|  | Comparative Example | | | |
| --- | --- | --- | --- | --- |
|  | 1 | 2 | 3 | 4 |
| Polyol ® TS30 | 93.3 | 93.3 |  |  |
| Polyol ® TP30 |  |  | 81 | 81 |
| IPDI trimer | 105 |  |  | 105 |
| HDI trimer |  | 63 | 63 |  |
| Butylacetate | 40 | 53 | 52.7 | 34.7 |

In all comparative examples the mixture gelled.

Example 9

Synthesis of Bis Hydroxyl Functional Urethane Intermediate With Tertiary Urethane Bond Following the procedure of example 1–3, 117 parts of n-butyl aminoethanol were reacted with 104 parts of propylene carbonate in 52 parts of n-butylacetate. After heating for about 10 hours at 110° C., the amine value was 16.

Comparative Example 5

Synthesis of a Bis Hydroxyl Functional Urethane With Secondary Urethane Bond

Following the procedure of examples 1–3 a bis hydroxyl functional urethane was prepared according to U.S. Pat. No. 4,820,830 by reacting 75 parts of isopropanol amine with 90 parts of propylene carbonate in 46 parts of n-butylacetate. After heating for about 5 hours the amine value was about 10.

Examples 10–11

Reaction of Bis Hydroxyl Functional Intermediate Example 9 With Polyisocyanates to Form a Branched Urethane Oligomers Following the procedure of examples 4–8, 1050 parts (example 10) of the cyclotrimer of isophoronediisocyanate (IPDI trimer, available from Creanova-Huls under IPDI T-1890) or 630 parts (example 11) of the cyclotrimer of hexamethylenediisocyanate (HDI trimer, available from Bayer under Desmodur® 3390) were reacted with 819 parts of the reaction product of example 9 in 119 parts (example 10) or 299 parts (example 11) of n-butylacetate.

|  | Test results: | |
| --- | --- | --- |
|  | Example 10 | Example 11 |
| Solids: | 69.3 | 67.2 |
| Viscosity: | Z6 – 1/4 | Z4 – 1/4 |
| Number av MW | 2500 | 3700 |
| Weight av MW | 7400 | 9800 |
| Dispersity | 3 | 2.6 |

Comparative Examples 6–7

Reaction of Bis Hydroxyl Functional Intermediate Comparative Example 5 With Polyisocyanates The procedure of example 10 and 11 was followed replacing the 819 parts of reaction product example 9 on a molar basis with 633 parts of reaction product comparative example 5 in 63 parts (comparative 6) or 193 parts (comparative 7) of n-butylacetate. In both comparative examples an insoluble reaction product was formed.

Comparative Example 8

Hydroxyl Functional Binder With Urea Linkages

One mole of the cyclotrimer of hexamethylenediisocyanate (HDI trimer, available from Bayer under Desmodur® 3390) was reacted with 3 mols of diisopropanol amine at 25% overall solids content in n-butylacetate to form a hydroxyl functional urea derivative. The reaction product was not soluble in n-butylacetate.

Example 12

Polyether Containing Reaction Product With Tertiary Urethane Bonds

Following the procedure as described in the second part of example 12, 1000 grams of Terathane® 1000 (a polytetramethylene glycol for DuPont) are reacted with 444 grams of isophorone diisocyanate in 599.86 grams (+18 grams for rinsing) butylacetate and 0.14 grams of dibutyltindilaurate. The mixture was held at 50° C. until an isocyanate % of 3.7% followed by 266 grams reaction product from example 1 and a rinsing of 114 grams butylacetate.

|  | Test results: Example 12 |
| --- | --- |
| Solids | 70.5 |
| Viscosity | Z2 |
| Number av MW | 5000 |
| Weight av MW | 7900 |

Example 13

Polyether Containing Reaction Product With Tertiary Urethane Bonds

The procedure of example 12 was followed but the Terathane 1000 was replaced by polypropyleneglycol with a molecular weight of 1000. The intermediate isocyanate content was 3.5%.

|  | Test results: Example 13 |
| --- | --- |
| Solids | 69.5 |
| Viscosity | G + 1/3 |
| Number av MW | 2100 |
| Weight av MW | 3200 |

Example 14

Polycarbonate Containing Reaction Product With Tertiary Urethane Bonds

The procedure of example 13 was followed but the Terathane® 1000 was replaced by a polycarbonate with a molecular weight of 1000 known under Ravecarb® 102 from Enichem. The intermediate isocyanate content was 4%.

| Test results: Example 14 | |
|---|---|
| Solids | 70.8 |
| Viscosity | Y |
| Number av MW | 3400 |
| Weight av MW | 7700 |

Example 15–16

Two-component Clear Coat

A clear coat was prepared by mixing following ingredients (weight basis)

| | Example 15 | Example 16 |
|---|---|---|
| Acrylic polyol[1] | 83.29 | 83.29 |
| Methyl isobutyl ketone | 4.47 | 4.47 |
| Primary amyl acetate | 2.36 | 2.36 |
| Ethyl 3-ethoxypropionate | 3.43 | 3.43 |
| Propyleneglycol methyl ether | 0.68 | 0.68 |
| Butyl acetate | 0.3 | 0.3 |
| Byk 306 (Byk chemie) | 0.05 | 0.05 |
| Byk 332 (Byk chemie) | 0.1 | 0.1 |
| Byk 361 (Byk chemie) | 0.2 | 0.2 |
| 1% dibutyltin dilaurate in xylene | 1.49 | 1.49 |
| Diethylethanol amine | 0.25 | 0.25 |
| Tinuvin 292 (Ciba) | 0.3 | 0.3 |
| Tinuvin 1130 (Ciba) | 0.6 | 0.6 |
| Acetic acid | 0.3 | 0.3 |
| Example 4 | 106 | |
| Example 10 | | 81.6 |
| Activator[2] | 120 | 82 |

Notes:
[1]47.7% solids in Solvesso ® 100 (Exxon), butylacetate, xylene = 18/22/10, OH value = 145, weight av molecular weight = 8000
[2]This blend was mixed with an activator containing Desmodur ® 3390 (Bayer) with an isocyanate percentage on activator of 12.8%

Both formulations have a ratio of hydroxyl/isocyanate equivalents=1.05.

The clear coats were sprayed over a conventional solvent borne basecoat at a dry film build of 60 microns and baked for 30 minutes at 60 C.

| Film properties | | |
|---|---|---|
| | Example 15 | Example 16 |
| Gloss at 20 angle | 82.5 | 85.2 |
| Distincness of image | 91.5 | 92.4 |
| Tack free time | 90 minutes | immediate |
| Hardness Fisher 1 day/1 week (knoops) | 7.7/19.9 | 6.5/18.5 |
| Hardness Persoz 1 day/1 week (seconds) | 225/347 | 192/330 |

Example 17

One Component Clear Coat

A clear coat was prepared by mixing following ingredients (weight basis)

| | |
|---|---|
| Acrylic polyol[1] | 9.97 |
| Modified Acrylic polyol[2] | 18.52 |
| Luwipal ® 018 (butylated melamine resin from BASF) | 21.49 |
| Byk 325 (Byk chemie) | 0.12 |
| Tinuvin ® 292 (Ciba) | 0.51 |
| Tinuvin ® 1130 (Ciba) | 1.02 |
| Irganox ® 1010 (Ciba) (30% in butylacetate) | 0.35 |
| Rheomet ® TTA (Ciba) (33% in isopropanol) | 0.17 |
| Dodecylbenzenesulfonic acid (35% in isopropanol/isobutanol = 15/50) | 1.31 |
| Example 4 | 28.86 |
| Butylacetate | 5 |
| Solvesso ® 100 | 10.68 |
| Solvesso ® 150 | 2 |

Notes:
[1]65% solids in Solvesso ® 100 (Exxon), Solvesso ® 150 (Exxon) = 18/16, OH value = 145, weight av molecular weight = 6000)
[2]Acrylic polyol modified with a anti-sag control agent based on a bis urea adduct of benzylamine/hexamethylenediisocyanate = 2/1 molar (55.7% solids in Solvesso ® 100/Solvesso ® 150 = 63/24 containing 5% on solids of the bis-urea)

The clear coat was diluted to spray viscosity with a blend of Solvesso® 100/Solvesso® 150=1/1 and sprayed over a conventional solvent borne basecoat at a dry film build of 40 microns and baked for 30 minutes at 145° C. The panel was aged for 24 hours at room temperature.

| Film properties | |
|---|---|
| Gloss at 20° angle | 91.7 |
| Hardness Fisher (knoops) | 16.3 |
| Hardness Persoz (seconds) | 221 |
| Xylene resistance | more than 5 minutes |
| Scratch resistance | very good |
| Sulfuric acid (10%) resistance | very good |

What is claimed is:

1. A hydroxy functional urethane compound comprising the reaction product of:
   a) a hydroxy functional urethane intermediate containing a tertiary carbamate group prepared by reaction of a cyclic 5-ring carbonate with a beta-hydroxy functional, secondary amine, said intermediate represented by the formula:

$$HO-\underset{\underset{R_3}{|}}{\overset{\overset{R_1}{|}}{CH}}-\overset{\overset{R_2}{|}}{CH}-N-\overset{\overset{O}{\|}}{C}-O-\overset{\overset{R_4}{|}}{CH}-\overset{\overset{R_5}{|}}{CH}-OH$$

wherein
$R_1$ and $R_2$=hydrogen, an alkyl of 1–4 carbon atoms, cycloalkyl or $R_6$—O—, $R_6$—CO—O— or $R_6$ optionally substituted with $R_6$—O— or $R_6$—CO—O—;
$R_6$=an alkyl, cycloalkyl or benzylic group having up to 18 carbon atoms;

$R_4$ and $R_5$=hydrogen or alkyl group optionally containing a hydroxyl group; and $R_3$=alkyl, cycloalkyl or benzylic group optionally containing an ether linkage and/or a hydroxyl group, or HO—CH($R_1$)—CH($R_2$)—; with b) a compound having at least 2 isocyanate groups;

wherein said hydroxy functional urethane intermediate of a) and said compound having at least 2 isocyanate groups of b) has an OH:NCO ratio ranging from 2:1 to 4:1: and further wherein the hydroxy functional urethane compound produced is free from isocyanate groups.

2. The urethane compound of claim 1, wherein the compound having at least two isocyanate groups is selected from the groups consisting of hexamethylene diisocyanates, isophorone diisocyanate, toluene diisocyanate, 3,3',5-trimethyl hexamethylene diisocyanate, meta and para tetramethyl xylene diisocyanate, 4,4'-dicyclohexylmethane diisocyanate, 4,4'-diphenylmethane diisocyanate, cyclotrimer of isophorone diisocyanate, cyclotrimer of hexamethylene diisocyanate, biuret of hexamethylene diisocyanate, uretdiondimer of hexamethylene diisocyanate, adducts of polyols and excess diisocyanates, and mixtures thereof.

3. The urethane compound of claim 1, wherein said hydroxy functional urethane intermediate of a) and said compound having at least 2 isocyanate groups of b) has an OH:NCO ratio of 3:1.

4. A coating composition comprising a hydroxy functional urethane compound comprising the reaction product of:

a) a hydroxy functional urethane intermediate containing a tertiary carbamate group prepared by reaction of a cyclic 5-ring carbonate with a beta-hydroxy functional, secondary amine, said intermediate represented by the formula:

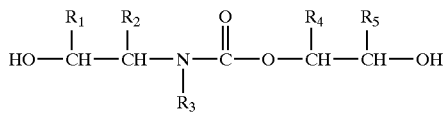

wherein $R_1$ and $R_2$=hydrogen, an alkyl of 1–4 carbon atoms, cycloalkyl or $R_6$—O—, $R_6$—CO—O— or $R_6$ optionally substituted with $R_6$—O— or $R_6$—CO—O—;

$R_6$=an alkyl, cycloalkyl or benzylic group having up to 18 carbon atoms;

$R_4$ and $R_5$=hydrogen or alkyl group optionally containing a hydroxyl group; and $R_3$=alkyl, cycloalkyl or benzylic group optionally containing an ether linkage and/or a hydroxyl group, or HO—CH($R_1$)—CH($R_2$)—; with b) a compound with at least 2 isocyanate groups;

wherein said hydroxy functional urethane intermediate of a) and said compound having at least 2 isocyanate groups of b) has an OH:NCO ratio ranging from 2:1 to 4:1: and further wherein the hydroxy functional urethane compound produced is free from isocyanate groups.

5. The coating composition of claim 4, wherein the compound having at least two isocyanate groups is selected from the groups consisting of hexamethylene diisocyanate, isophorone diisocyanate, toluene diisocyanate, 3,3',5-trimethyl hexamethylene diisocyanate, meta and para tetramethyl xylene diisocyanate, 4,4'-dicyclohexylmethane diisocyanate, 4,4'-diphenylmethane diisocyanate, cyclotrimer of isophorone diisocyanate, cyclotrimer of hexamethylene diisocyanate, biuret of hexamethylene diisocyanate, uretdiondimer of hexamethylene diisocyanate, adducts of polyols and excess diisocyanates, and mixtures thereof.

6. The coating composition of claim 4, further comprising a curing agent selected from the group consisting of melamine formaldehyde adducts etherified with an alcohol selected from methanol, isobutanol and n-butanol, methylethyl ketoxime blocked trimer of hexamethylene diisocyanate, methylethyl ketoxime blocked trimer of isophorone diisocyanate, dimethyl pyrazole blocked trimer of hexamethylene diisocyanate, dimethyl pyrazole blocked trimer of isophorone diisocyanate, biuret of hexamethylene diisocyanate, cyclotrimer of hexamethylene diisocyanate, biuret of isophorone diisocyanate, and cyclotrimer of isophorone diisocyanate.

7. The coating composition of claim 4, wherein said hydroxy functional urethane intermediate of a) and said compound having at least 2 isocyanate groups of b) has an OH:NCO ratio of 3:1.

* * * * *